(12) United States Patent
Richard

(10) Patent No.: US 6,178,622 B1
(45) Date of Patent: Jan. 30, 2001

(54) DEVICE FOR ASSEMBLING A NEEDLE AND A SUTURE THREAD INCLUDING MEANS FOR EXTRACTING ONE SUTURE THREAD FROM A BUNDLE OF SUCH THREADS

(75) Inventor: François Richard, Leves (FR)

(73) Assignee: Ethicon S.A.S. (FR)

( * ) Notice: Under 35 U.S.C. 154(b), the term of this patent shall be extended for 0 days.

(21) Appl. No.: 09/196,815

(22) Filed: Nov. 20, 1998

(51) Int. Cl.[7] .................................................. B23P 19/00
(52) U.S. Cl. ................... 29/822; 29/715; 29/788; 29/796; 53/430
(58) Field of Search ..................... 53/430; 29/822, 29/715, 788, 796

(56) References Cited

U.S. PATENT DOCUMENTS

| | | | |
|---|---|---|---|
| 4,419,859 | * | 12/1983 | Mima ......................................... 57/22 |
| 4,722,384 | * | 2/1988 | Matsutani .................................. 163/1 |
| 5,664,404 | * | 9/1997 | Ivanov et al. ............................ 53/430 |

\* cited by examiner

*Primary Examiner*—David P. Bryant

(57) ABSTRACT

The invention provides a device for assembling a urgical needle (700) and a suture thread (110, 115), the device comprising an extractor device (300, 400, 500) for extracting one segment of suture thread (110, 115) from a bundle (100) of segments (110, 115) the extractor device (300, 400, 500) comprising means (322, 324, 400) suitable for displacing segments (110, 115) by air flowing transversely to the longitudinal direction of the bundle, a suction inlet (322, 324) suitable for being placed laterally relative to the bundle (100), and two sliding surfaces (310) suitable for guiding one segment (110, 115) to the suction orifice (322, 324) when the segments (110, 115) are displaced by the flow of air.

10 Claims, 3 Drawing Sheets

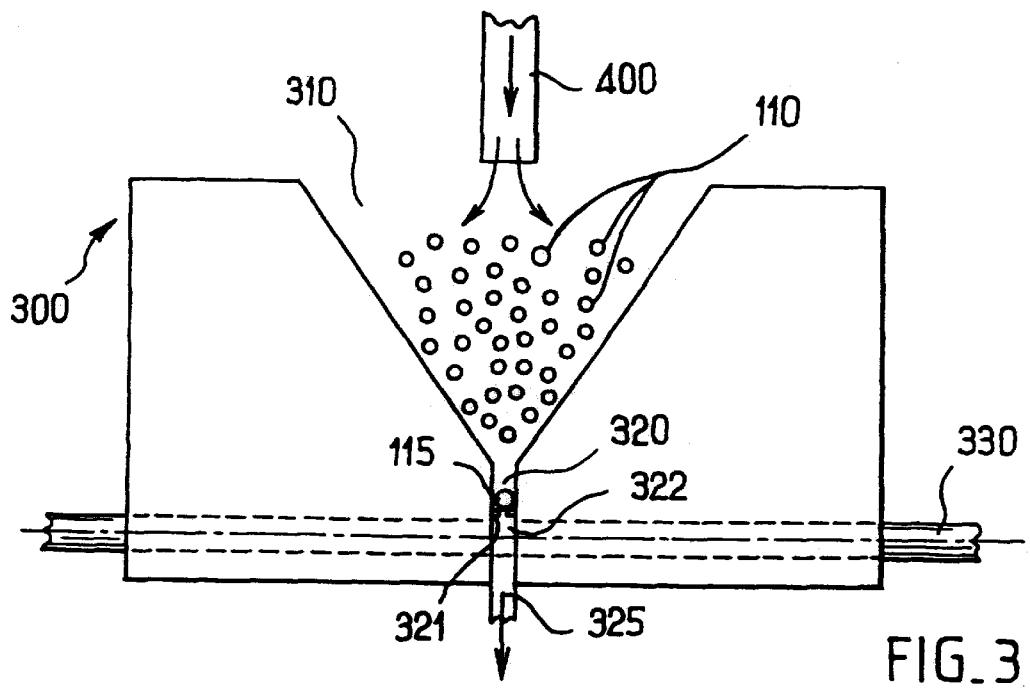
FIG_3
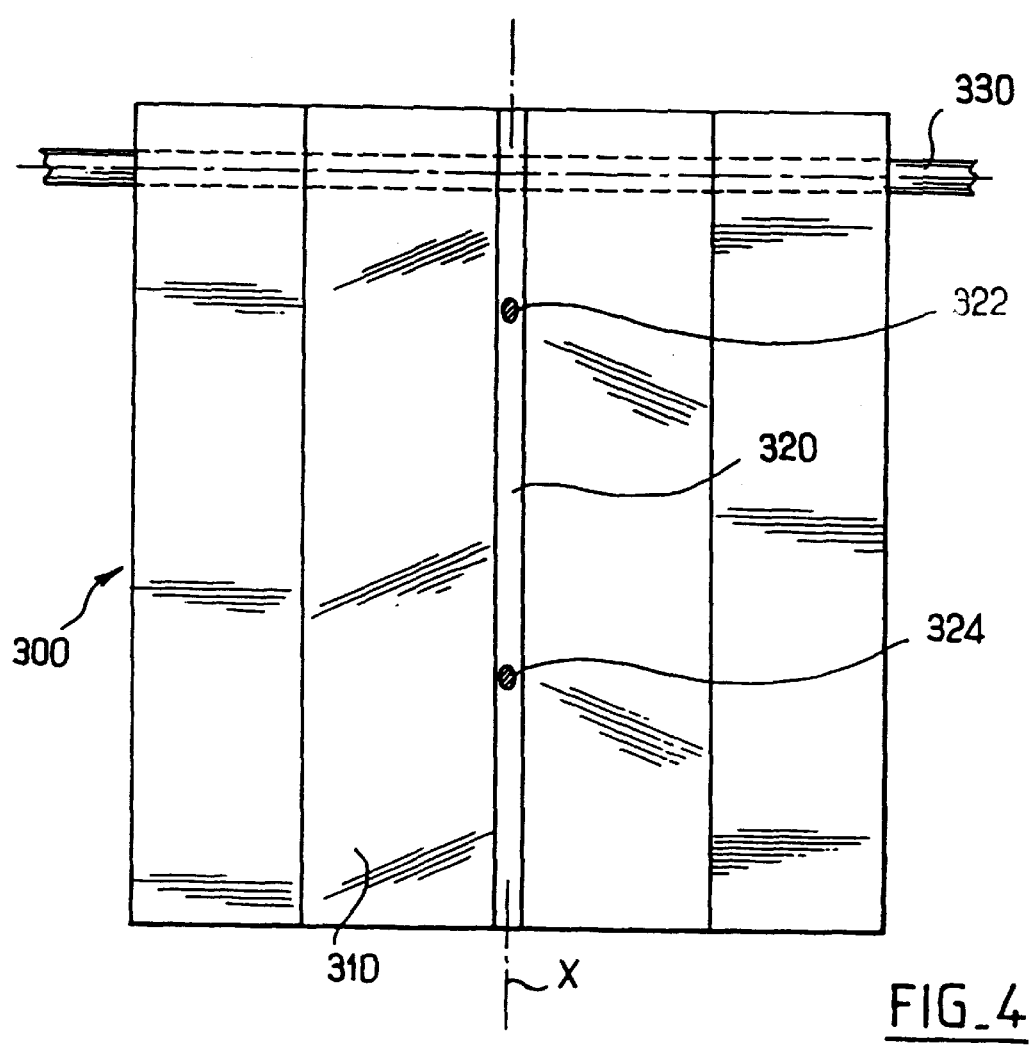
FIG_4

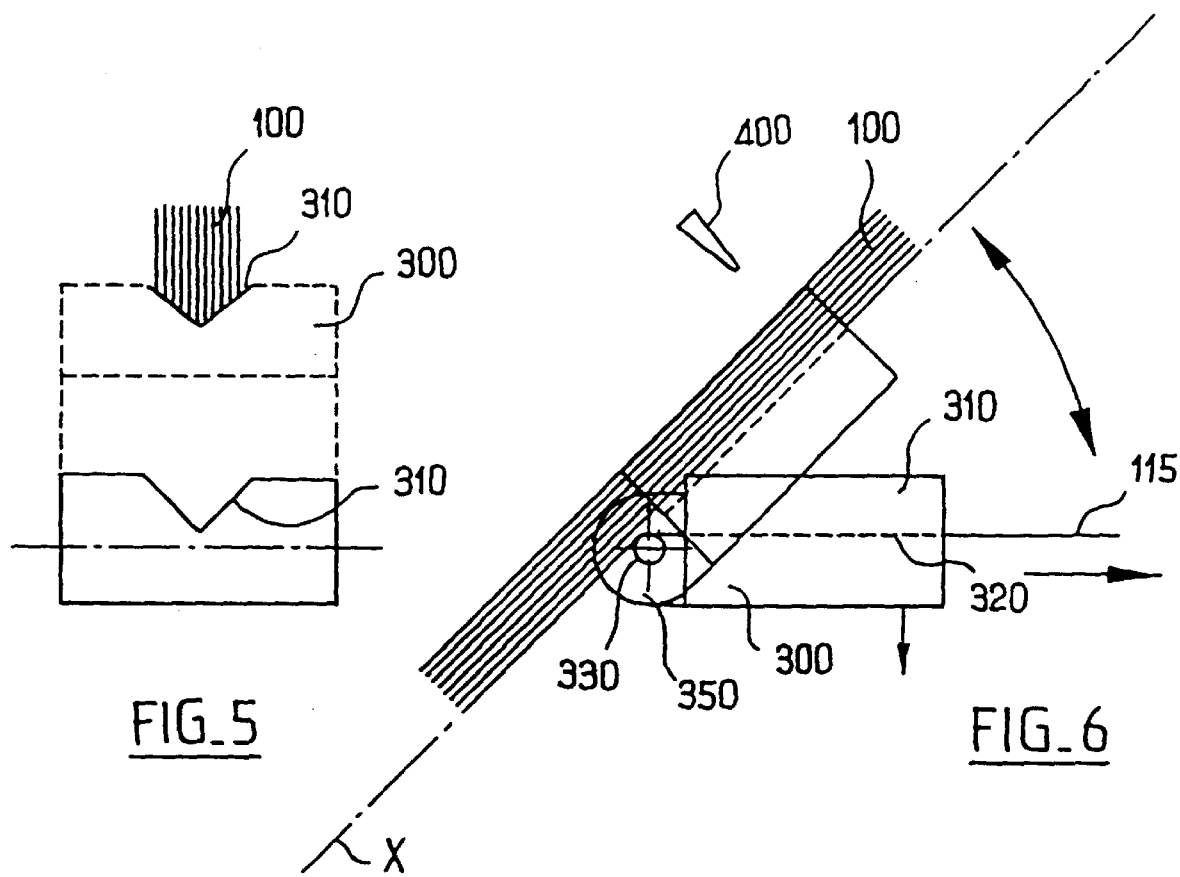
FIG_5　　FIG_6
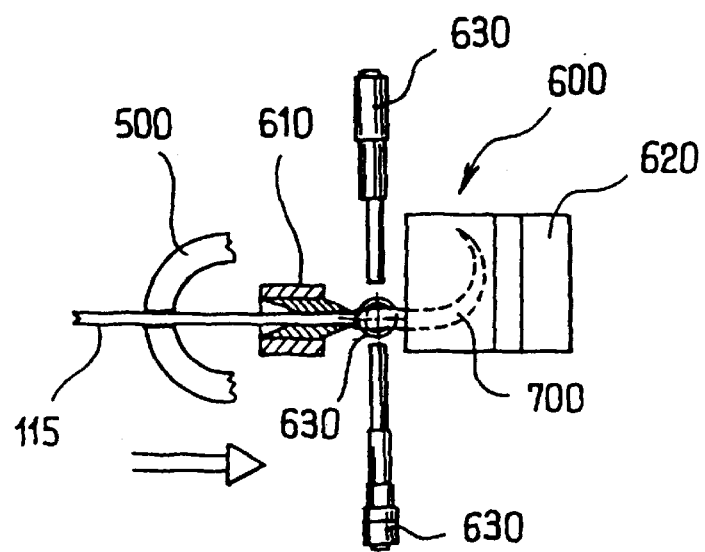
FIG_7

DEVICE FOR ASSEMBLING A NEEDLE AND A SUTURE THREAD INCLUDING MEANS FOR EXTRACTING ONE SUTURE THREAD FROM A BUNDLE OF SUCH THREADS

The present invention relates to the field of devices enabling a surgical needle and a suture thread to be assembled together.

Numerous devices have already been proposed for securing a needle to a suture thread.

U.S. Pat. No. 4,922,904 thus proposes a device for connecting a suture to a needle, which device automatically inserts one end of a suture thread into a surgical needle, presses the needle in such a manner as to pinch the thread in the needle, and then cuts the suture thread to a predetermined length.

In general, automated devices for assembling needles and suture thread are designed to fix the thread in the needle before cutting the thread at a selected location, between the needle and a reel on which the thread is stored prior to assembly.

Such devices suffer from a major drawback.

Being stored on a reel gives the thread an arcuate rest shape which is troublesome while handling the thread when performing a suture operation. More precisely, arcuate threads tend to roll up onto themselves and to move elastically into or in front of the wound where being sutured.

It is therefore preferable to use threads that tend to take up a rectilinear shape. That is why proposals have been made to provide such reel devices with means for heating the thread so as to give it a rectilinear rest shape. Such heater means give rise to expensive production costs and such heating tends to weaken the suture thread.

Proposals have already been made to use suture threads that are precut to lengths close to their length after assembly, and for them to be stored in rectilinear manner in a bundle, sheaf, or skein.

That type of storage also makes it possible to store the same total length of thread in a smaller space than when using reel storage.

Also, each time a reel is changed, reel devices require the thread to be threaded through the device, which is difficult to do and requires the tension of the thread along its path between the reel and the needle to be watched constantly.

Proposals have therefore also been made for devices that assemble suture thread with needles that are adapted to insert, in a needle, a segment of thread that has been precut to its final length.

Thus, U.S. Pat. No. 4,722,384 discloses a device which is used as follows. An operator manually inserts one end of a segment of suture thread in a needle, and then places the needle fitted with the suture thread inside the device and actuates a control pedal of the device to crimp the needle onto the suture thread.

Those devices suffer from the major drawback of requiring an operator to take hold of one segment only from the bundle of segments, and to bring it to the needle before inserting it in the needle.

The operation of extracting one segment only from a collection of segments turns out to be very trying for an operator. On each assembly, the operator must first fix attention on the sheaf of segments, then on the needle and the end of one segment. On each assembly, the operator must therefore look closely at two different zones situated at two different distances from the eyes, and that gives rise very rapidly to a high degree of eye fatigue.

More generally, devices for assembling needles and suture thread provided in the form of precut segments require human intervention. As a result they are slow and present high production costs.

The main aim of the present invention is to propose a device for assembling needles and suture thread which is fed with suture thread in the form of a bundle or sheaf of segments, and which automatically extracts a single segment of suture thread from the bundle of segments.

Another object of the invention is to propose a device for assembling surgical needles and segments of suture thread which operates without human intervention.

According to the present invention, these objects are achieved by a device for assembling a surgical needle and a suture thread, comprising an extractor device for extracting one segment of suture thread from a bundle of segments, the extractor device comprising means suitable for displacing segments by air flowing transversely to the longitudinal direction of the bundle, a suction inlet suitable for being placed laterally relative to the bundle, and two sliding surfaces suitable for guiding one segment to the suction inlet when the segments are displaced by the flow of air.

In an advantageous but non-limiting disposition, a device is provided in which the suction inlet is constituted by an element that is movable between a first position in which the inlet is close enough to the bundle to receive one segment thereagainst under the effect of its suction on its own or assisted by other air flows generated by the device, and a second position that is further away from the bundle.

The invention also provides a method of assembling a surgical needle and a segment of suture thread using such a device, the method comprising the steps consisting in:

placing said element in its first position;

moving segments of the bundle against the sliding surfaces by means of a flow of air and sucking one segment against the suction inlet;

moving said element into its second position while maintaining sufficient suction to ensure that the segment remains pressed against the suction inlet;

taking hold of the segment and engaging it in a surgical needle; and fixing the surgical needle on the segment.

Other characteristics, objects, and advantages of the invention appear on reading the following detailed description, given by way of example with reference to the accompanying drawings, in which:

FIG. 3 is a section view through an extractor device of the present invention in an extraction or first position, shown on a section plane extending transversely to a main direction of a bundle of segments;

FIG. 4 is a plan view of a pivot arm of an extractor device of the present invention;

FIG. 5 is a view of an extractor device of the present invention seen from a point towards which a segment points when it is entrained by a pivot arm to a second position of the arm, in accordance with the present invention;

FIG. 6 is a side view of the same extractor device as is shown in FIG. 5; and

FIG. 7 is a side view of a device of the invention for moving a segment of suture thread and automatically fixing it to a needle.

Figures 1, 2:
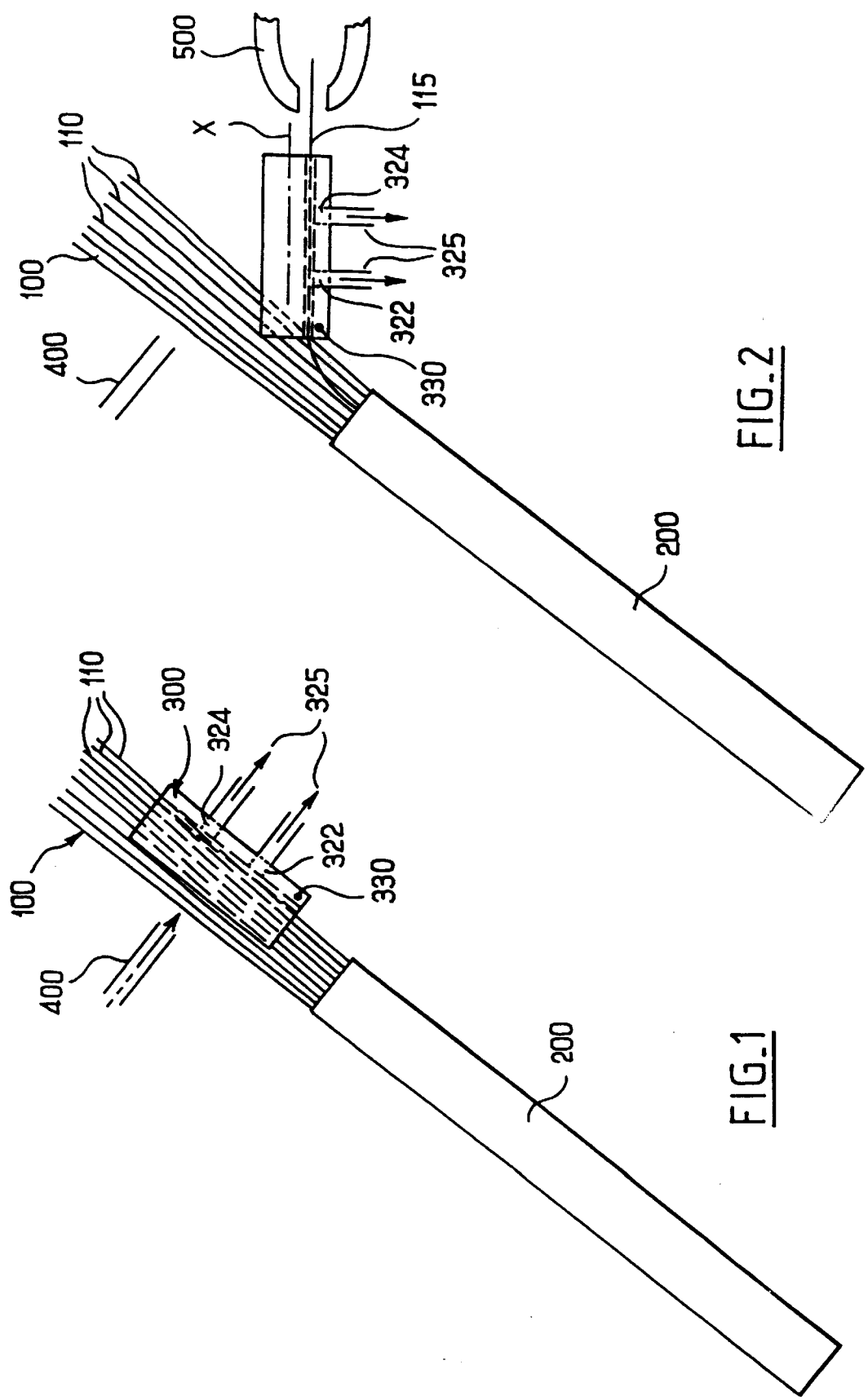
FIG. 1 is a side view of an automatic extractor device of the invention with a pivot arm of the invention in a first position.
FIG. 2 is a side view of the same assembly in a second position of the pivot arm, and also showing a clamp for taking a segment.

In FIGS. 1 and 2, there can be seen a bundle of segments 100 disposed in a quiver 200.

The segments of the bundle 100 may be constituted, for example, by polypropylene suture threads having a length of about 40 cm.

The quiver 200 is of rectangular cross-section. It is disposed so as to be at an angle of about 45° relative to the vertical, its closed end being at the bottom end of the quiver.

More precisely, two of the side faces of the quiver are parallel to a plane containing the vertical and the main axis of the quiver, while its other two side faces are perpendicular to said plane.

The width and the length of the quiver 200 are selected as a function of the segments and of their bending stiffness. It is desired that the segments should project from the top portion of the quiver in the form of a bundle or sheaf, i.e. that the segments in said zone should be substantially rectilinear and substantially parallel to one another. Thus, it is possible with increasing bending stiffness of the segments to increase the length of the bundle projecting from the quiver.

In the example described herein, a quiver of length equal to two-thirds the length of the segments enables them to maintain their rectilinear shape in their portions projecting from the quiver 200.

A quiver that is of a width substantially equal to one-tenth of its length makes it possible to guarantee that the segments remain substantially parallel to one another regardless of the degree to which the quiver is filled.

FIGS. 1 to 4 show a pivot extractor arm 300.

As can be seen in FIGS. 3 and 4, the arm essentially comprises a slightly flattened piece generally in the shape of a parallelepiped and extending in a main direction X.

A top face of the pivot arm 300 has a trough 310 extending along the central portion of said face in the main direction X of the arm 300 over the entire length of the arm 300.

The trough 310 has the same cross-section along its entire length. This cross-section is V-shaped, with the limbs of the V being at an angle of about 45° to each other.

The trough 310 is open in the top face of the arm 300 over an opening width that is substantially equal to half the total width of the pivot arm 300, and the depth of the trough 310 is substantially equal to said opening width.

The bottom of the trough 310 has a groove 320 which extends along the entire length of the trough 310. In a cross-section of the trough 310, the groove 320 thus extends the tip of the V away from the top face, i.e. towards the bottom of the arm 300.

The groove 320 is narrow and shallow compared with the width and the depth of the trough 310.

In the bottom of the groove 320, there are disposed two suction orifices 322 and 324.

As can be seen in particular in FIGS. 1 and 2, the arm 300 is mounted to pivot on a fixed axis 330 extending transversely thereto in a direction that is transverse to the main direction X of the pivot arm 300. The axis 330 passes through the arm 300 below the groove 310 and close to one of the ends of the arm 300.

The axis 330 extends perpendicularly to the main direction of the quiver 200 and it is level in the bundle direction with that portion of the bundle 300 which projects from the quiver 200.

The arm 300 is positioned on the axis 330 so that when the arm 300 is pivoted about the axis 330 to take up an orientation parallel to the quiver 200 while presenting its end through which the axis 330 passes to the quiver 200, its main trough 310 is open towards the bundle 100.

The axis 300 is also located at a distance from a main axis of the quiver 200 such that when the arm 300 is in the position described above, the main trough 310 receives a portion of the bundle 100 between its sloping portions. Thus, as shown in FIG. 3, segments 110 run along the arm 300 in its main trough 310.

In addition, the axis 330 is located in the longitudinal direction of the bundle 100 at a distance from the top end of the bundle which is sufficient to ensure that the segments received between the sloping portions of the main trough 310 travel not only along the full length of the through, but also have their top ends projecting significantly beyond the arm 300.

The arm 300 is suitable for pivoting from this first position to a second position in which its main direction X extends horizontally, as shown in FIG. 2.

As can be seen in FIG. 3, the groove 320 at the bottom of the through 310 is of a width that is substantially equal to the diameter of the segments 110.

The groove 320 is also of a depth that is equal to about two or three segments diameters.

The bottom of the groove 320 is constituted by a substantially plane bottom wall 321 that may alternatively have a cross-section that is arcuate, complementary to the outline of a segment. This wall is provided with two suction inlets or orifices 322 and 324 each communicating with a suction tube 325 connected to a source of suction. Each of these two orifices is circular in section having a diameter that is smaller than the diameter of a segment.

In FIGS. 1 to 3, there can also be seen a blow nozzle 400 disposed so as to be diametrically opposite the arm 300 about a main axis of the bundle 100.

The elements described above constitute an extractor device for extracting a single segment 110 from the bundle 100. The extractor device operates as follows.

Initially, the pivoting arm 300 is placed parallel to the bundle 100, as shown in FIG. 1. In this position, some of the segments in the bundle are received between the sloping portions of the main trough 310. More precisely, the bottom of the trough 310 forming a top inlet to the groove 320 is in alignment with a bottom face of the quiver.

Thus, as can be seen in FIG. 3, segments 110 are to be found in the main trough 310 in the vicinity of the top inlet to the groove 320. At this stage, no segment is to be found in the groove 320 itself.

Then, the suction source connected to the orifices 322 and 324 is set into operation and simultaneously air is blown through the blow nozzle 400 towards the bundle 100. This flow of air produces thrust on the segments of the bundle, urging them towards the bottom of the main trough 310, with the segment closest to the groove 320 also being subjected to the flow of air that is sucked in through the two orifices 322 and 324.

Under the combined effect of blowing from the nozzle 400 and suction through the nozzles 322 and 324, one of the segments 115 penetrates into the groove 320. The segment 115 moves under the effect of this suction until it is pressed against the bottom wall 321.

Since the width of the groove 320 is substantially equal to the diameter of the segments 110, it is not possible for two segments to move towards the bottom wall 321, side by side.

More generally, the groove 320 is advantageously, but not necessarily, designed to be of a width lying between the diameter of a segment 110 and twice the diameter of a segment 110, so that two segments 110 cannot enter and move down the groove 320 side by side. Thus, it is guaranteed that a single segment 115 is extracted from the bundle 100 in any one operating cycle of the device.

Also, the groove 320 is advantageously selected to be narrow in width so that suction through the orifices 322 and 324 as channeled specifically by a single segment, provides effective suction without requiring a large amount of suction power.

Once the segment 115 is pressed against the bottom wall, it closes the two orifices 322 and 324. The segment 115 is then held pressed against the bottom wall 321 by suction applied to its bottom outline through the orifices 322 and 324, while it simultaneously stops any flow of air passing through the orifices 322 and 324.

Thus, no other segment continues to be sucked into the bottom of the groove 320, and, because of their elasticity, the segments contained in the trough 310 remain outside the groove 320, whether or not air is being blown from the nozzle 400.

Thereafter, while maintaining suction through the orifices 322 and 324, the arm 300 is pivoted to its second position. The segment 115 remains in the bottom of the groove 320 and is thus entrained with the arm.

With the arm 300 in its horizontal or second position, the portion of the segment 115 initially projecting from the quiver 200 is separated from the other segments in the bundle 100 to occupy a horizontal position, and it is held in this horizontal position by suction through the orifices 322 and 324.

As described above, when the arm is in its second position, the segment 115 projects beyond the end of the arm 300 that is remote from the quiver 200, and that is therefore also remote from the bundle 100.

FIGS. 5 and 6 show a pivot arm 300 constituting a variant of the invention. In this variant, the groove 320 is disposed so that a line extending the bottom of the groove is tangential to the outline of the pin on the axis 330, with the axis 330 being below said line, i.e. going away from the top face of the arm 300.

In addition, the axis 330 passes through the arm 300 in a rounded base portion 350 of the arm 300 that constitutes an extension of the arm extending towards the bundle when the arm 300 is in its horizontal position.

The trough 310 of V-shaped section does not extend over the base portion 350.

In addition, in a portion of the arm 300 that is in line with the trough 310, the base portion leaves the pin on the axis 330 uncovered such that when the arm 300 is in its horizontal position, the segment 115 bears against the pin on the axis 330. Under such circumstances, the segment 115 constitutes two rectilinear portions of opposite sides of the pin, with these two segment portions being interconnected by a portion that bears against the outline of the pin on the axis 330 and therefore presents curvature no greater than the curvature of the circular outline of the pin.

The segment 115 is thus not subjected to any edge or sharp corner in the zone where it is curved, and as a result the segment is not subjected to any significant amount of folding which could give it a curved rest shape.

In FIGS. 2 and 7, there can be seen a clamp 500 for taking hold of the end of the segment 115 that projects from the arm 300 and then moving said segment away from the quiver 200.

The clamp 500 is advantageously mounted to slide on a slide rail, with its movements along the rail and the opening and closing thereof being under electrical control so as to be synchronized with the movements of the arm 300.

The clamp 500 takes hold of the segment 115 at a point close to the end of the arm that is remote from the bundle, and entrains it to a device for fixing a needle to a suture thread, referenced 600 in FIG. 7.

This device is of conventional type and comprises a funnel 610 for guiding the suture thread, a holding piece 620 for holding a needle in line with the suture thread, and punches 630 for crimping the needle.

In conventional manner, a needle 700 is conveyed automatically into alignment with a narrow outlet from the funnel 620, so that the needle presents a rear orifice facing said narrow outlet from the funnel 610. The needle is held securely in this position by the holding piece 620.

The clamp 500 entrains the segment 115 towards the device 600, inserting an end of the segment into the funnel 610, which in turn guides the segment into the needle 700.

The punches 630 which are located on opposite sides of the needle 700 are directed towards the portion of the needle which is suitable for receiving the segment 115. Once the segment 115 has been inserted into the needle 700, the punches 630 press against the needle so that it pinches the segment 115 and holds it permanently in place. The assembly constituted by the needle 700 and the segment 115 can then be released by the device 600.

The description above relates to a device for automatically assembling a segment of suture thread and a surgical needle, which device does not require human intervention. Naturally, the invention is not limited to such devices, but also extends to devices that are not fully automated.

Thus, the invention provides a device in which the segments are extracted one by one from a bundle of segments by an automatic device having a pivoting suction arm as described above, and in which an operator takes hold of each extracted segment and inserts it by hand into a needle, and then places the needle together with its segment in a conventional device for crimping the needle onto the segment.

What is claimed is:

1. A device adapted for use with an apparatus for assembling a surgical needle and a suture thread, the device comprising an extractor device for extracting one segment of suture thread from a bundle of segments, the extractor device comprising means suitable for displacing segments by air flowing transversely to the longitudinal direction of the bundle, a suction inlet suitable for being placed laterally relative to the bundle, said suction inlet being located at the bottom of a cavity of width that is greater than the diameter of said segment and less than twice the diameter of said segment, and two sliding surfaces suitable for guiding one segment to the suction inlet when the segments are displaced by the flow of air.

2. A device according to claim 1, wherein the suction inlet is of section that is small enough to be closed by a segment pressing thereagainst.

3. A device according to claim 1, wherein the sliding surfaces are suitable for forming a V-outline transversely to the bundle of segments, the suction inlet being at the bottom of the V-shape.

4. A device according to claim 1, wherein the cavity is in the form of a groove suitable for extending substantially parallel to the bundle of segments.

5. A device according to claim 1, wherein the device has a plurality of suction inlets.

6. A device according to any claim 1, wherein the suction inlet is constituted by an element that is movable between a first position in which the inlet is close enough to the bundle to receive one segment thereagainst under the effect of its suction on its own or assisted by other air flows generated by the device, and a second position that is further away from the bundle.

7. A device according to the claim 5, wherein said element is mounted to pivot about an axis perpendicular to the main direction of the bundle.

8. A device according to claim 1, wherein the device has a blow nozzle diametrically opposite to the suction inlet about a main axis of the bundle, the blow nozzle being directed towards the bundle.

9. A device according to claim 1, wherein the device includes a quiver designed to receive a fraction of the length of the bundle, and in that the quiver is inclined relative to the vertical.

10. A device according to claim 9, wherein the device is situated beneath a portion of the bundle that projects from the quiver.

* * * * *